ns Patent [19]

Juvinall et al.

[11] Patent Number: 4,601,395
[45] Date of Patent: Jul. 22, 1986

[54] INSPECTING AND SORTING OF GLASS CONTAINERS

[75] Inventors: John W. Juvinall, Ottawa Lake, Mich.; Sam Lovalenti; William H. Rogge, both of Toledo, Ohio

[73] Assignee: Owens-Illinois, Inc., Toledo, Ohio

[21] Appl. No.: 602,862

[22] Filed: Apr. 23, 1984

[51] Int. Cl.$^4$ .................. B07C 5/342; G01N 21/32
[52] U.S. Cl. .................... 209/526; 209/939; 250/223 B; 356/240; 356/428; 358/106
[58] Field of Search .................. 209/522–524, 209/526, 538, 555, 556, 558, 588, 939; 250/223 B; 356/240, 428; 350/314; 358/106

[56] References Cited

U.S. PATENT DOCUMENTS

| | | | |
|---|---|---|---|
| 3,030,516 | 4/1962 | Seavey | 209/526 X |
| 3,094,214 | 6/1963 | Wyman et al. | 209/524 |
| 3,356,853 | 12/1967 | Rottman | 209/526 X |
| 3,411,009 | 11/1968 | Ford et al. | 209/524 X |
| 3,529,898 | 9/1970 | De Mey, II | 350/314 |
| 3,651,937 | 3/1972 | Kronseder | 209/526 X |
| 3,746,429 | 7/1973 | Spindel et al. | 350/314 |
| 3,981,565 | 9/1976 | Karasawa | 350/314 X |
| 4,378,493 | 3/1983 | Dorf et al. | 250/223 B |
| 4,402,612 | 9/1983 | Alexander et al. | 356/240 X |
| 4,487,322 | 12/1984 | Juvinall | 209/526 |

Primary Examiner—Robert B. Reeves
Assistant Examiner—Edward M. Wacyra
Attorney, Agent, or Firm—John R. Nelson

[57] ABSTRACT

A method and apparatus for inspecting and sorting transparent containers such as glass containers having defects in the container sidewalls, and for distinguishing between commercially acceptable and unacceptable defects on the basis of defect type and size. A light source is positioned to direct diffused illumination through the sidewall of a container under inspection as the container is rotated about its central axis with the intensity of the illumination varying across the light source transversely of such axis as a predetermined function of transverse position. In specific disclosed embodiments of the invention, the light intensity is filtered across the source to provide transversely spaced outer regions of uniform intensities, either equal or unequal, and an intermediate region of either uniform intensity different from that in the outer regions or transversely varying intensity. A camera which includes a plurality of light sensitive elements disposed in a linear array parallel to the axis of container rotation is positioned to receive light energy transmitted through the container sidewall. Electronics monitor the camera light elements during container rotation, identifies defects as a function of differences in light detected by the camera elements at adjacent increments of container rotation, and generates signals to distinguish and sort defective containers from commercially acceptable containers. A conveyor sequentially presents containers for inspection and includes separate selectable exit paths for acceptable and unacceptable containers.

27 Claims, 27 Drawing Figures

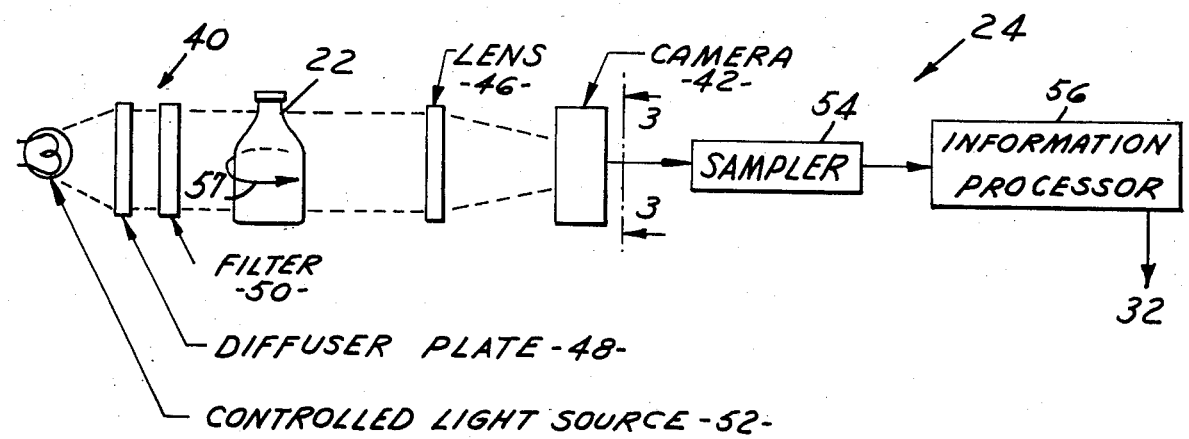
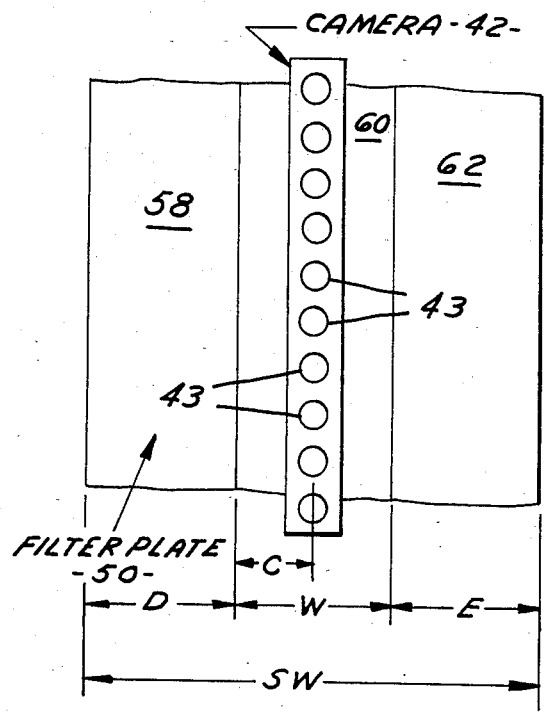

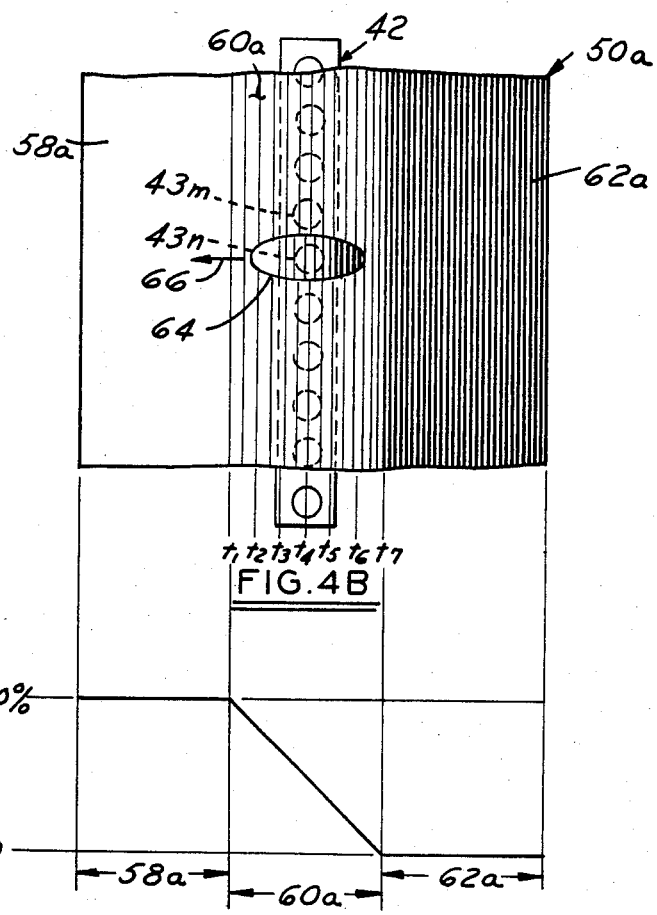
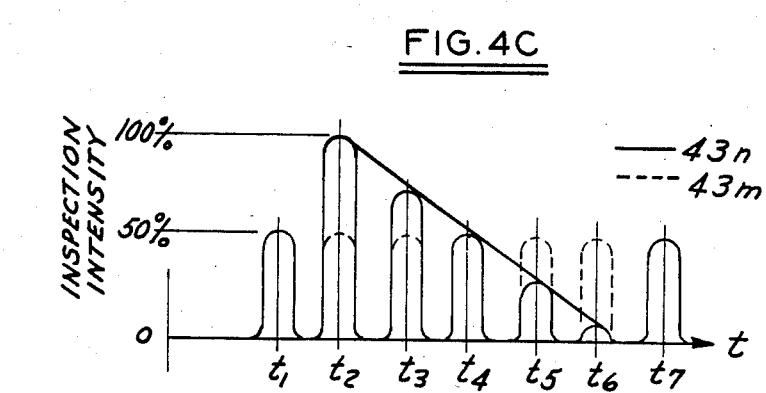
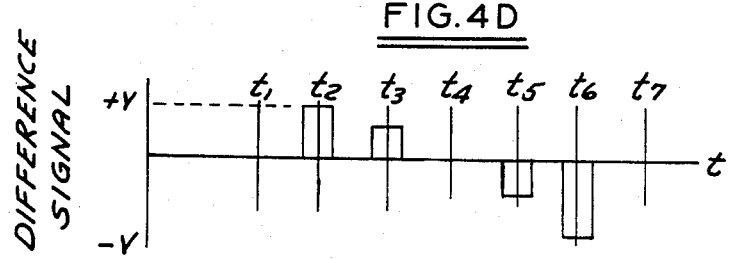

INSPECTING AND SORTING OF GLASS CONTAINERS

The present invention is directed to inspecting and sorting of transparent containers for defects in the container sidewalls; and more particularly to inspection of glass containers for refractive sidewall defects such as blisters and/or opaque sidewall defects such as stones, and selective sorting of containers having defects so detected.

BACKGROUND OF THE INVENTION

In the manufacture of glass containers, various types of defects may occur. It has heretofore been proposed to employ optical scanning techniques for inspecting such containers for defects which affect optical transmission characteristics of the container sidewall. In U.S. Pat. Nos. 4,378,493, 4,378,494 and 4,378,495, all of which are assigned to the assignee of the present application, there is disclosed a method and apparatus in which glass containers are conveyed through a plurality of positions or stations where they are physically and optically inspected. At one optical inspection station, a glass container is held in vertical orientation and rotated about its vertical central axis. An illumination source directs diffused light energy through the container sidewall. A camera, which includes a plurality of light sensitive elements, i.e., pixels, oriented in a linear array parallel to the vertical axis of container rotation, is positioned to view light transmitted through a vertical strip of the container sidewall. The output of each pixel is sampled at increments of container rotation, and event signals are generated when the magnitude of adjacent pixel signals differ by more than a preselected threshold level. An appropriate reject signal is thus produced and the defective container is sorted from the conveyor line.

The method and apparatus disclosed in the aforementioned patents, commonly referred to as the Sidewall Inspection Device (SID), have been found to be very effective and efficient for general automated inspecting and sorting of glass containers. However, some problems have been encountered in using the SID for detecting certain specific types of defects. For example, to enhance detection of refractive defects which are transverse to the container axis, such as ribbon tear defects, it has been proposed in U.S. application Ser. No. 424,687 filed Sept. 27, 1982, now U.S. Pat. No. 4,487,322, to direct a filtered source of diffused light toward the sidewall of the container which provides a longitudinal illumination intensity gradient which varies in the direction of the vertical strip field of view of the camera, and thus substantially parallel with the axis of the container. The intensity of light is sensed and defect signals are generated as a function of differences between intensities at successive light sensitive elements within the camera. Defective containers are then sorted from the conveyor line. The technique so proposed has been employed successfully for reliable and efficient detection of transverse ribbon tear defects and sorting of containers having such defects.

Problems have also been encountered in using the SID for distinguishing among types and sizes of defects. For example, the SID employs a wide source of light energy which is wide enough so that most refracted defects do not refract light enough to be visible as a dark spot on the bright background of the wide source. However, because opaque defects absorb light energy, they are visible as dark spots on the bright background of the wide source. In other words, the SID detects opaque defects but is generally blind to refractive defects. The instant invention is directed to the problem of detecting the presence of an opaque defect, while at the same time being able to detect refractive defects by optical enhancement and further distinguish between small refractive defects, such as small blisters in the container sidewall, and large refractive defects, such as large blisters. It is important in the manufacture of glass containers to be able to identify major refractive defects such as large blisters as well as opaque defects, both of which may become sites for incipient crack propagation leading ultimately to fracture of the container. On the other hand, small refractive defects, such as small blisters in the container sidewall, are commercially acceptable and should not be rejected. These problems have been especially prevalent in the manufacture of narrow-neck containers such as beer bottles. Sorting and rejecting containers having commercially acceptable defects is inefficient and increases the manufacturing cost. Therefore, there is a need for an improved technique for reliably detecting commercially unacceptable defects while distinguishing such defects from otherwise commercially acceptable defects, and then for sorting and rejecting only those containers having commercially unacceptable defects.

OBJECTS AND SUMMARY OF THE INVENTION

It is therefore an object of the present invention to provide an improved method and apparatus for inspecting and sorting transparent containers, particularly glass containers, which are economical to implement, which embody the proven technology disclosed in the aforementioned patents and application, which are capable of readily distinguishing character and size of sidewall defects, and which are effective for sorting containers having commercially unacceptable defects while passing containers having commercially acceptable defects. Therefore, it is also an object of the invention to provide character recognition for individual defects.

In accordance with the present invention, a transparent container is inspected and sorted for defects in the container sidewall by rotating the container about its central axis while directing through the sidewall of the container diffused light having an intensity gradient which varies across the light source in a direction transverse to the axis of container rotation as a predetermined function of position in such transverse direction. A camera is positioned to monitor light energy transmitted through the container sidewall within a narrow strip field of view parallel to the container axis of rotation. The type of sidewall defect is determined as a function of the magnitude of the events produced by the pixels of the camera, and the size of the defect so identified is determined as a function of the location of the same events. Containers having unacceptable defects, such as large blisters or stones, are rejected and automatically sorted from acceptable containers.

More specifically, in the various embodiments of the invention herein disclosed, the intensity of light transmitted through the container toward the camera is controlled as a function of transverse position across the source of diffused illumination to provide first and second, transversely spaced, outer zones of substantially uniform illumination intensities, and a third central zone between such first and second zones in which the intensity of diffused illumination is different from the intensities in the adjacent outer zones. Illumination intensities in the outer zones may be at differing levels or at substantially identical levels. Where the intensities in the outer zones are at differing levels, the intensity in the central zone may vary uniformly, linearly or logarithmically, between such differing intensity levels, or may be at a substantially uniform intensity level intermediate the differing intensity levels in the outer zones. In the most preferred embodiment of the invention, the intensities within the first and second outer zones are at substantially equal uniform levels, and the intensity within the central zone is likewise substantially uniform and at a level different from that within the outer zones.

DESCRIPTION OF THE DRAWINGS

FIG. 2 is an electrical and optical functional block diagram of the invention.

FIG. 3 is a fragmentary schematic diagram of the optical system in FIG. 2 as viewed along the line 3—3 in FIG. 2.

FIGS. 4A and 5A are schematic diagrams similar to that of FIG. 3 illustrating one embodiment of the invention, and FIGS. 4B–4D and 5B–5D are graphic illustrations useful in describing the structure and operation of the embodiment of FIGS. 4A and 5A.

DESCRIPTION

The disclosures of the above-noted U.S. Pat. Nos. 4,378,493, 4,378,494 and 4,378,495, all issued Mar. 29, 1983, to the assignee of the present application, and the disclosure of the above-noted U.S. application Ser. No. 424,687, filed Sept. 27, 1982 and assigned to the assignee of the present application, are all incorporated herein by reference.

Figure 1:
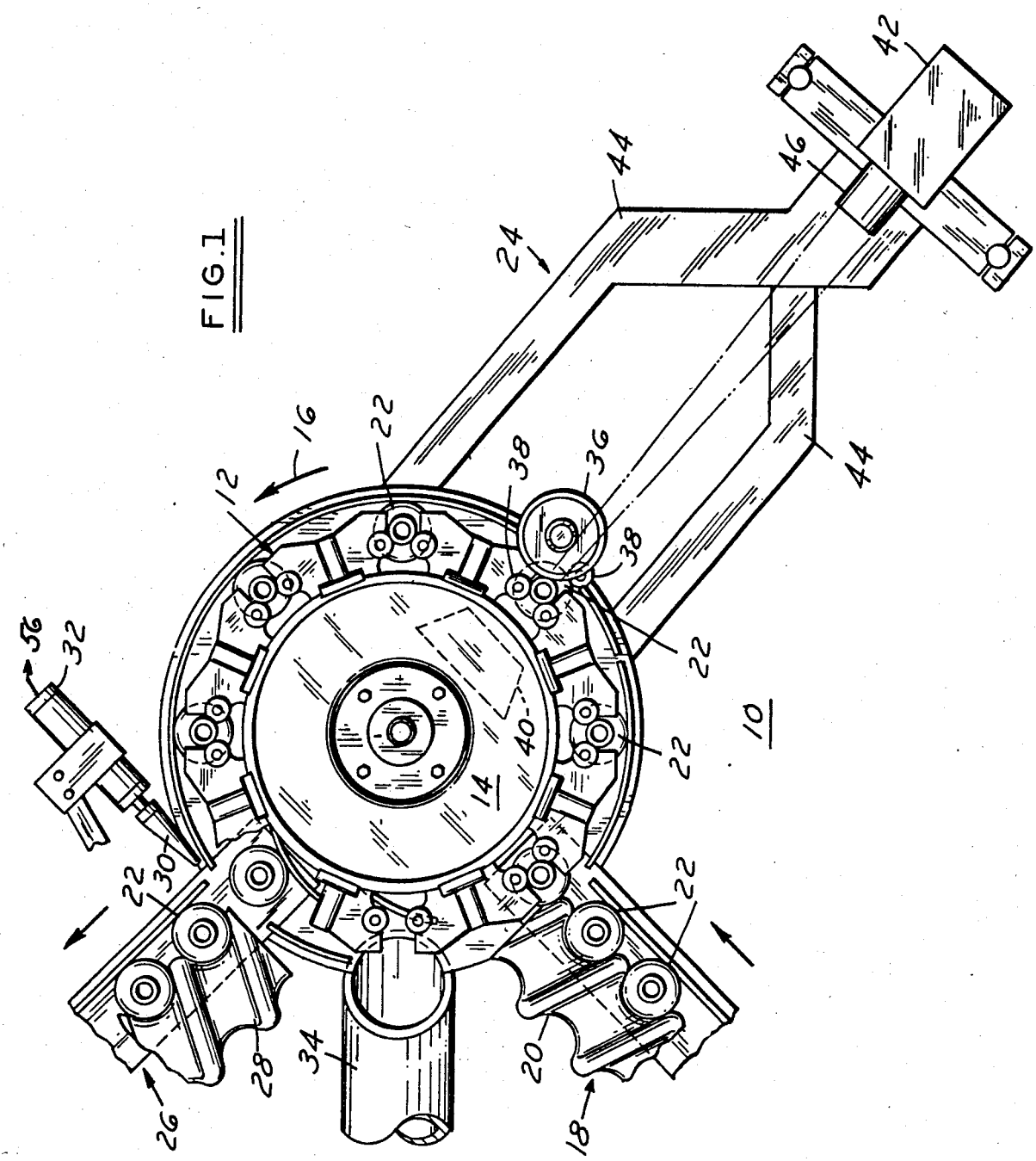
FIG. 1 is a plan view of a container inspection system in which the invention is employed.

FIG. 1 is a fragmentary plan view of a container inspection system 10 which includes a starwheel 12 coupled to a drive hub 14 for step-wise rotation in a counterclockwise direction indicated by the arrow 16. A feed conveyor 18 includes a driven screw 20 for feeding transparent containers 22, such as glass containers, in upright orientation to the periphery of starwheel 12. Starwheel 12 conveys containers 22 in an arcuate path through a plurality of inspection stations, only one of which is illustrated in detail at 24. A discharge conveyor 26 includes a driven screw 28 which receives containers 22 from the periphery of starwheel 12 after each container has been moved by the starwheel through the plurality of inspection stations. A plunger 30 is coupled to a solenoid 32 and is disposed to block exit to discharge conveyor 26 when actuated by the solenoid. In the event that an unacceptable defect has been detected in a particular container at any of the inspection stations, plunger 30 is actuated by solenoid 32 to block exit to conveyor 26 when that container is rotated to a position adjacent to such exit, so that the defective container is thereafter conveyed by starwheel 12 to a reject discharge chute 34.

The present invention relates to the inspection station which is illustrated at station 24. Station 24 includes a drive roller 36 positioned to engage a container 22 and to rotate the container in a counterclockwise direction while the container 22 is held in fixed axial position by the idler rollers 38. A light source 40 is positioned within the periphery of starwheel 12 beneath the plane of hub 14 and directs diffused light energy radially outwardly to illuminate the full height and width of the container sidewall while the container is rotated about its axis by drive roller 36. A camera 42 is positioned by the brackets 44 radially outwardly of light source 40 and starwheel 12. Camera 42 includes a plurality of light sensitive elements or pixels 43 (FIG. 3), preferably two hundred fifty-six, disposed in a linear array parallel to the vertical axis of rotation of container 22 at station 24 and aligned with such axis and the vertical centerline of light source 40. A lens 46 focuses a vertical strip of the container sidewall onto the element array. To the extent thus far described, inspection system 10 and inspection station 24 are similar to those disclosed in the aforementioned patents, and reference is made thereto for a more detailed description of the mechanical structure of the inspection system.

Light source 40 as disclosed in the aforementioned patents comprises a plurality of incandescent lamps disposed in three columns parallel to the axis of container rotation. A diffuser plate is positioned between the lamp array and the container, so that diffused illumination from a relatively wide light source is directed onto and through the container sidewall to lens 46 and camera 42. Sampling electronics compares signals from adjacent pixels of the linear array and provides an event signal to an information processor when such signals from adjacent pixels differ by more than a preselected threshold level. The information processor electronics then operates solenoid 32 and plunger 30 when the associated defective container moves to the inspection station exit position, so that the defective container is sorted to the reject chute 34 as previously described. As indicated above, such inspection and sorting technique has been quite effective and successful, but has encountered problems associated with distinguishing among types and sizes of defects. The present invention is directed toward solution of these difficulties.

FIGS. 2 and 3 are electro-optical schematic and functional block diagrams of a presently preferred embodiment of the invention at inspection station 24. Within light source 40, which is illustrated in plan view in FIG. 1 and in side elevation at FIG. 2, a diffuser plate 48 and an intensity filter plate 50 are positioned to intercept and direct light energy from a source 52 of illumination through the sidewall of a container 22 and through lens 46 onto camera 42.

Sampling electronics 54 receives signals from each pixel 43 (FIG. 3) within camera 42 and provides strings of serial signals to the information processor 56. The container 22 is rotated in a direction indicated by the arrow 56 at a speed controlled as a function of the rotational speed of the inspection system 10 to insure that the camera 42 provides a predetermined number of scans per container, e.g., 300 strings or scans per container. The sampling in electronics 54 is correspondingly adjustable. The information processor 56 generates an event signal when the magnitude of signals from adjacent pixels in a scan differ by more than a preselected threshold. It will be appreciated that the term "adjacent pixels" contemplate distinct elements which are in physical proximity to each other within the linear array of the camera 42. The information processor 56 performs a connectivity analysis by evaluating the locations of a plurality of events to determine whether a defect is present. Based on this analysis, the processor 56 controls operation of the solenoid 32 (FIG. 2) and the plunger 30 for sorting defective containers.

FIG. 3 is a fragmentary view in side elevation which schematically illustrates filter plate 50 and the relationship of camera 42 thereto as viewed in the direction 3—3 in FIG. 2. In accordance with the present invention for enhanced detection of and discrimination among sizes and types of sidewall defects, the optical density of filter plate 50 is varied across the width SW of illumination source 40, i.e., transversely of the container axis of rotation, to provide a non-isotropic illumination intensity distribution along the transverse dimension. In the specific embodiment of the invention herein disclosed, the optical density of filter plate 50 is selected to provide at least two laterally adjacent illumination zones 60,62, and preferably three laterally adjacent illumination zones 58,60,62 across the width SW of source 40. The optical densities of adjacent zones 58,60 and 60,62 differ from each other. The centerline of camera 42 is aligned with the midline of the central zone 60 positioned between the outer zones 58,62. With no container 22 present between lens 46 and source 40, or with a container having no sidewall defects positioned and rotated between the lens and illumination source, the intensity of illumination incident upon camera elements 43 is primarily a function of the optical density at the midline of central zone 60. However, when a refractive sidewall defect such as a blister is moved in front of the camera, such defect refracts the field of view of the pixels 43 within the camera 42 along a refracted path to outer zone 58 or outer zone 62. The present invention utilizes the controlled variation in transverse illumination intensity to distinguish types and sizes of defects.

FIGS. 4A and 4B, which possess identical horizontal position scales, illustrate one embodiment of the invention. FIG. 4A is a fragmentary view similar to that of FIG. 3, and FIG. 4B graphically illustrates optical density of filter plate 50a (FIG. 4A) as a function of transverse position. In the embodiment of FIGS. 4A and 4B, optical attenuation density in outer zone 58a of the filter plate 50a is substantially zero, or transparent, while the attenuation density of outer zone 62a is substantially one hundred percent or opaque. Within central zone 60a, the optical density varies linearly between substantially zero at the lateral edge contiguous with outer zone 58a and substantially one hundred percent at the edge contiguous with outer zone 62a.

The sampling electronics 54 receives signals from each pixel 43 within the camera 42 and provides a signal from each one serially to generate a string of pixel signals during each scan of the linear array of the camera 42 at a time t. A blister defect 64 is shown in the field of view of a pixel 43n during several scans at times $t_2$ to $t_6$. The horizontal scale of FIG. 4C shows the scan time-increments $t_1$ to $t_7$ and relates them to actual blister position. Thus, the scan at time $t_1$ occurs just before the blister 64 rotates into the field of view of pixel 43n and the scan at time $t_7$ occurs just after the blister 64 rotates out of the field of view of pixel 43n. The vertical scale of FIG. 4C shows the actual illumination intensity "seen" by pixel 43n for each scan as the blister 64 passes through its field of view. The sampling electronics 54 provides the string of pixel signals for each scan to the information processor 56 which generates an "event" signal when the magnitudes of adjacent pixel signals, e.g., from pixels 43n and 43m, in a scan differ by more than a predetermined threshold. FIG. 4D, which has the same horizontal time scale as does FIG. 4C, illustrates the corresponding "difference" signals generated by the information processor 56 and used to determine the presence of an event. The event occurs at a specific "location" on the sidewall of a container. The event location is defined by the scan number, which provides an indication of the angular position of the container as described above, and the pixel number which corresponds to the longitudinal position along the container sidewall. The present SID, as described in the above-incorporated patents, also performs a connectivity analysis by analyzing the locations of a pluraltiy of events to determine whether a defect is present.

In operation, the light intensity sensed by pixel 43n will vary as its field of view is refracted from the midline of the central zone 60a by the blister 64. Starting at scan time $t_1$, just before the blister 64 enters the field of view of the pixel 43, the intensity sensed by pixel 43n is at about the 50 percent level since the field of view of the pixel 43n is incident the midline of central zone 60a. Thus, the corresponding difference signal at scan time $t_1$ is essentially zero since the intensities sensed by adjacent pixels 43n and 43m are substantially the same. However, at scan time $t_2$, just as the leading edge of the blister 64 enters the field of view of pixel 43n while moving in direction 66 with respect to the stationery filter plate 50a and camera 42, the intensity sensed by pixel 43n increases to about the 100 percent level because the leading edge of the blister 64 optically refracts the field of view of pixel 43n into the essentially transparent outer zone 58a. The corresponding difference signal at scan time $t_2$ is a substantially positive value because the intensity sensed by pixel 43n is substantially greater than that sensed by pixel 43m. At scan time $t_3$, when the leading edge of the blister 64 moves further into the field of view of pixel 43n, the intensity sensed by pixel 43n increases only to about the 75 percent level because the refractive characteristics of the leading edge are less severe and refract the field of view of pixel 43n only as far as the outer region of central zone 60a. Thus, the corresponding difference signal at scan time $t_3$ is still a positive value because the intensity sensed by pixel 43n is still greater than that sensed by pixel 43m. At scan time $t_4$, just after the refractive leading edge of blister 64 moves out of the field of view of the pixel 43n, the intensity sensed by pixel 43n returns to about the 50 percent level since the essentially parallel faces of the blister 64 are no longer refracting the field of view of pixel 43n. Thus, the corresponding difference signal at scan time $t_4$ returns to zero. At scan time $t_5$, the trailing edge of the blister 64 begins to move into the field of view of pixel 43n. The intensity sensed decreases to about the 25 percent level because the refractive characteristics of the trailing edge are not so severe and refract the field of view of pixel 43n only as far as the outer region of central zone 60a. Thus, the corresponding difference signal at scan time $t_5$ becomes a negative value because the intensity sensed by pixel 43n is somewhat less than that sensed by pixel 43m. At scan time $t_6$, when the trailing edge of the blister 64 moves fully into the field of view of pixel 43n, the intensity sensed reduces to zero because the trailing edge of the blister 64 refracts the field of view into outer zone 62a which is essentially opaque. Thus, the corresponding difference signal at scan time $t_6$ has a substantially negative value because the intensity sensed by pixel 43n is substantially less than that sensed by pixel 43m. At scan time $t_7$, after the trailing edge of the blister 54 moves out of the field of view of the pixel 43n, the intensity sensed is again at about the 50 percent level because the field of view of pixel 43n is incident the midline of the central zone 60a rather than being refracted by a defect. Thus, the corresponding difference signal at scan time $t_7$ is essentially zero since the intensities sensed by pixels 43n and 43m are substantially the same.

As can be seen, the difference signals associated with a blister or any refractive defect produce a computer-identifiable signature which comprises a peak-positive value that reduces to a peak-negative value. The information processor 56 determines the size of the blister 64 by using the connectivity analysis referred to above which provides an indication of the transverse dimension of the blister 64 by counting the number of scans between the peak-positive and peak-negative difference signals corresponding to the leading and trailing edge, respectively, of the blister 64. The information processor 56 is programmed to provide a reject signal 32 when the number of scans exceeds a predetermined threshold indicating the presence of a large blister, so that containers with large blisters are rejected and containers with small blisters are not rejected as being commercially acceptable. The same analysis would be used and the same signature would be obtained if the blister 64 were large enough to interfere with the field of view of several pixels 43. A similar signature would be obtained for each pixel varying only in transverse length.

The instant invention not only gives the SID the capability to detect refractive defects by optical enhancement and further distinguish between small and large refractive defects, but also to retain the capability to detect opaque defects. The opaque defects absorb light energy and in the instant invention are visible as dark spots on a "gray" background. Essentially, the opaque defect will produce a different signature of difference signals than does a refractive defect. Referring to FIGS. 5A to 5D, an opaque defect or stone 68 is shown in the field of view of pixel 43n. In operation, the light intensity sensed by pixel 43n will vary as its field of view is blocked from the midline of the central zone 60a by the stone 68. At scan time $t_2$, just as the leading edge of the stone 68 enters the field of view of pixel 43n, the intensity sensed by pixel 43n drops to zero because the stone is opaque. Thus, the corresponding difference signal at scan time $t_2$ has a substantially negative value because the intensity sensed by pixel 43n is substantially less than that sensed by pixel 43m. The same analysis applies to the light intensity sensed by pixel 43n at scan times $t_3$ to $t_6$. Thus, the signature produced by the stone 68 is readily distinguishable from the signature produced by the blister 64; the signature of a blister is flanked by a peak-positive value and a peak-negative value while the signature of a stone consists solely of peak-negative values. Thus, this embodiment of the invention permits the SID to detect the presence of an opaque defect, while at the same time being able to detect refractive defects by optical enhancement and further distinguish between small and large refractive defects.

Figure 5A:
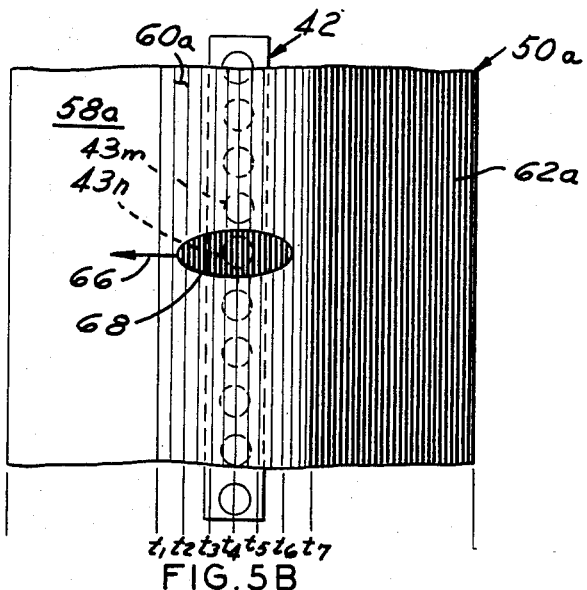
Figure 5B:
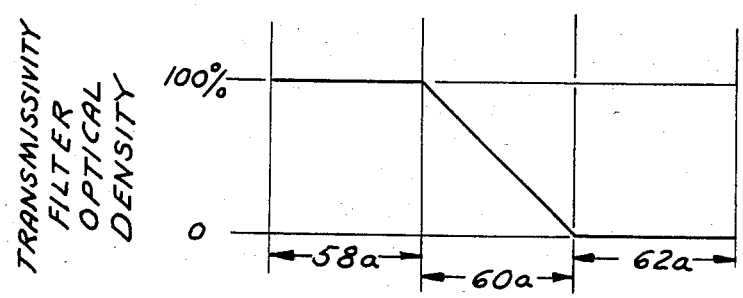
Figure 5C:
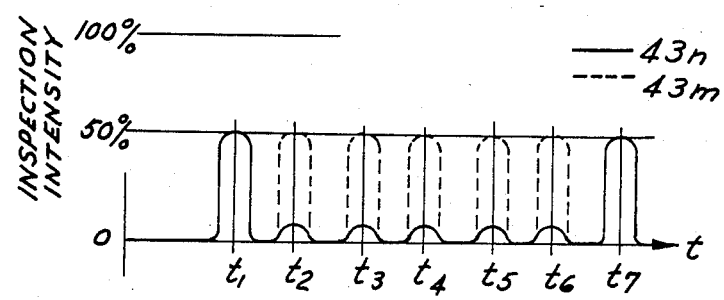
Figure 5D:
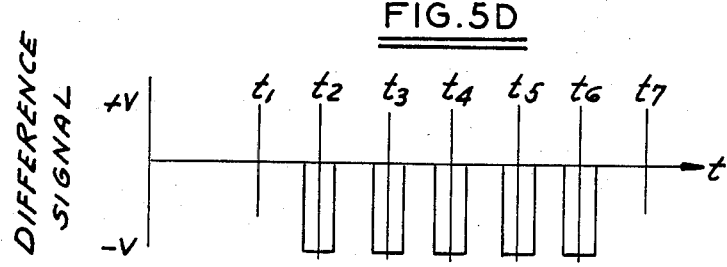
Figure 6A:
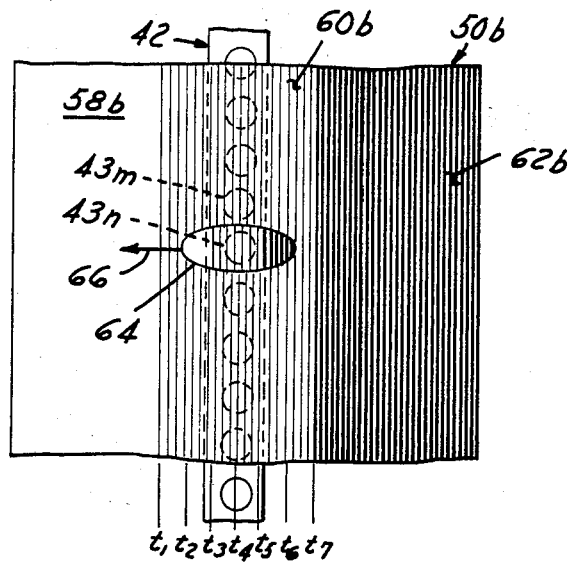
FIGS. 6A and 7A are schematic diagrams similar to that of FIG. 3 illustrating a modified embodiment of the invention.
Figure 6B:
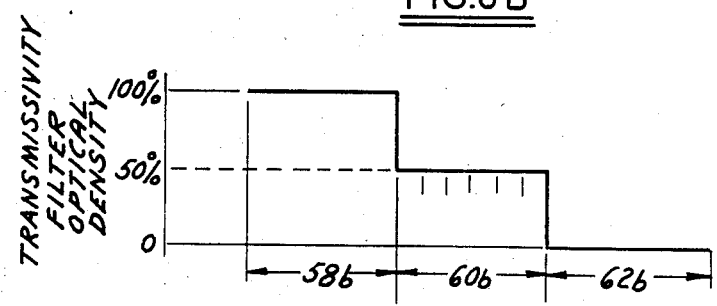
FIGS. 6B–6D and 7B–7D are corresponding graphic illustrations useful in describing operation of the embodiment of FIGS. 6A and 7A.

FIGS. 6A-6D and 7A-7D, which are respectively similar to FIGS. 4A-4D and 5A-5D, illustrate another embodiment of the invention. In FIGS. 6A and 6B, optical attenuation density in outer zone 58b of the filter plate 50b is substantially zero or transparent, while the attenuation density of outer zone 62b is substantially one hundred percent or opaque. Within central zone 60b, the optical density is subtantially fifty percent.

Figure 6C:
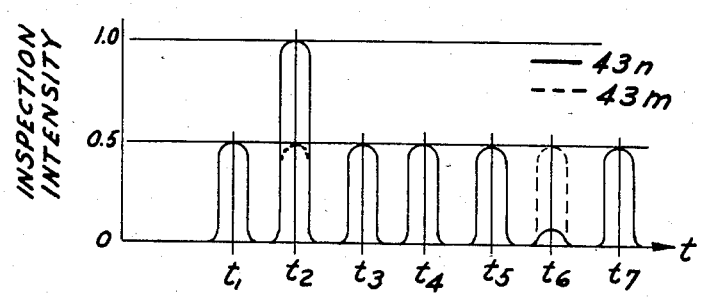
Figure 6D:
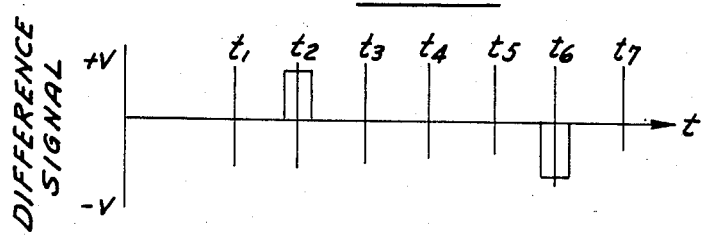

The sampling electronics 54 receives signals from each pixel 43 within the camera 42 and provides a signal from each one serially to generate a string of pixel signals during each scan of the linear array of the camera 42 at a time t. A blister defect 64 is shown in the field of view of a pixel 43n during several scans at times $t_2$ to $t_6$. The horizontal scale of FIG. 6C shows the scan time-increments $t_1$ to $t_7$ and relates them to actual blister position. Thus, the scan at time $t_1$ occurs just before the blister 64 rotates into the field of view of pixel 43n and the scan at time $t_7$ occurs just after the blister 64 rotates out of the field of view of pixel 43n. The vertical scale of FIG. 6C shows the actual illumination intensity "seen" by pixel 43n for each scan as the blister 64 passes through its field of view. The sampling electronics 54 provides the string of pixel signals for each scan to the information processor 56 which generates an "event" signal when the magnitudes of adjacent pixel signals, e.g., from pixels 43n and 43m, in a scan differ by more than a predetermined threshold. FIG. 6D, which has the same horizontal time scale as does FIG. 6C, illustrates the corresponding "difference" signals generated by the information processor 56 and used to determine the presence of an event. The event occurs at a specific "location" on the sidewall of a container. The event location is defined by the scan number, which provides an indication of the angular position of the container as described above, and the pixel number which corresponds to the longitudinal position along the container sidewall. The present SID, as described in the above-incorporated patents, also performs a connectivity analysis by analyzing the locations of a plurality of events to determine whether a defect is present.

In operation, the light intensity sensed by pixel 43n will vary as its field of view is refracted from the midline of the central zone 60b by the blister 64. Starting at scan time $t_1$, just before the blister 64 enters the field of view of the pixel 43n, the intensity sensed by pixel 43n is at about the 50 percent level since the field of view of the pixel 43n is incident the midline of central zone 60b. Thus, the corresponding difference signal at scan time $t_1$ is essentially zero since the intensities sensed by adjacent pixels 43n and 43m are substantially the same. However, at scan time $t_2$, just as the leading edge of the blister 64 enters the field of view of pixel 43n while moving in direction 66 with respect to the stationery filter plate 50b and camera 42, the intensity sensed by pixel 43n increases to about the 100 percent level because the leading edge of the blister 64 optically refracts the field of view of pixel 43n into the essentially transparent outer zone 58b. The corresponding difference signal at scan time $t_2$ is a substantially positive value because the intensity sensed by pixel 43n is substantially greater than that sensed by pixel 43m. At scan time $t_3$, when the leading edge of the blister 64 moves further into the field of view of pixel 43n, the intensity sensed by pixel 43n decreases to the 50 percent level. Thus, the corresponding difference signal at scan time $t_3$ is substantially zero because the intensity sensed by pixel 43n is about the same as that sensed by pixel 43m. The same remains true at times $t_4$ and $t_5$. At scan time $t_6$, when the trailing edge of the blister 64 moves fully into the field of view of pixel 43n, the intensity sensed reduces to zero because the trailing edge of the blister 64 refracts the field of view into outer zone 62b which is essentially opaque. Thus, the corresponding difference signal at scan time $t_6$ has a substantially negative value because the intensity sensed by pixel 43n is substantially less than that sensed by pixel 43m. At scan time $t_7$, after the trailing edge of the blister 64 moves out of the field of view of the pixel 43n, the intensity sensed is again at about the 50 percent level because the field of view of pixel 43n is incident the midline of central zone 60b rather than being refracted by a defect. Thus, the corresponding difference signal at scan time $t_7$ is essentially zero since the intensities sensed by pixels 43n and 43m are substantially the same. As was the case with FIGS. 4A–4D, the information processor 56 determines the size of the blister 64 by using the connectivity analysis referred to above which provides an indication of the transverse dimension of the blister 64 by counting the number of scans between the peak-positive and peak-negative difference signals corresponding to the leading and trailing edge, respectively, of the blister 64. The information processor 56 is programmed to provide a reject signal 32 when the number of scans exceeds a predetermined threshold indicating the presence of a large blister, so that containers with large blisters are rejected and containers with small blisters are not rejected as being commercially acceptable. The same analysis would be used and the same signature would be obtained if the blister 64 were large enough to interfere with the field of view for several pixels 43. A similar signature would be obtained for each pixel varying only in transverse length.

Referring to FIGS. 7A to 7D, an opaque defect or stone 68 is shown in the field of view of pixel 43n. In operation, the light intensity sensed by pixel 43n will vary as its field of view is blocked from the midline of the central zone 60b by the stone 68. At scan time $t_2$, just as the leading edge of the stone 68 enters the field of view of pixel 43n, the intensity sensed by pixel 43n drops to zero because the stone is opaque. Thus, the corresponding difference signal at scan time $t_2$ has a substantially negative value because the intensity sensed by pixel 43n is substantially less than that sensed by pixel 43m. The same analysis applies to the light intensity sensed by pixel 43n at scan times $t_3$ to $t_6$. Thus, the signature produced by the stone 68 is readily distinguishable from the signature produced by the blister 64; the signature of a blister is flanked by a peak-positive value and a peak-negative value while the signature of a stone consists solely of peak-negative values. Thus, this embodiment of the invention permits the SID to detect the presence of an opaque defect, while at the same time being able to detect refractive defects by optical enhancement and further distinguish between small and large refractive defects.

Figure 8A:
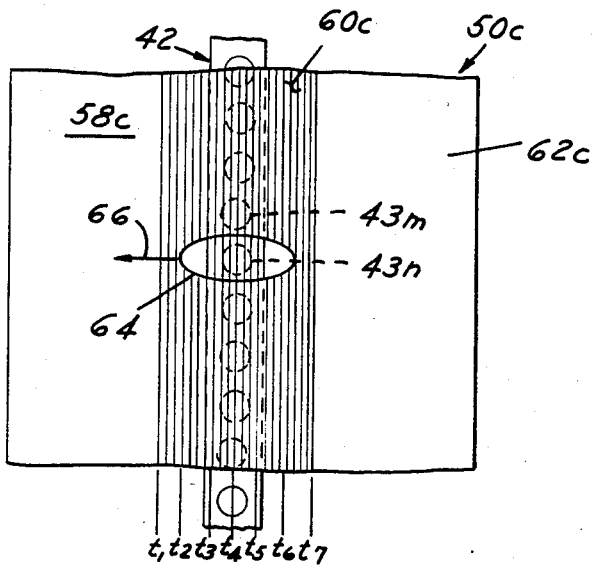
FIGS. 8A and 9A are schematic illustrations of a further embodiment of the invention.
Figure 8B:
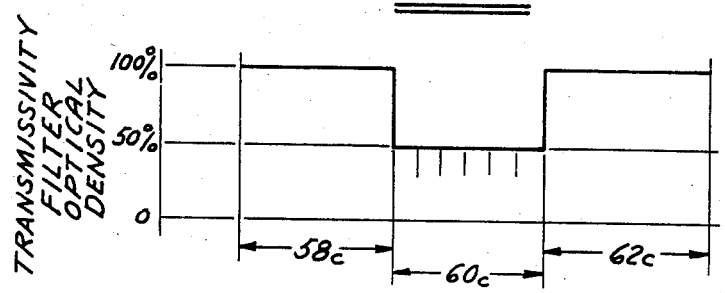
FIGS. 8B–8D and 9B–9D are corresponding graphic illustrations for describing the operation thereof.
Figure 8C:
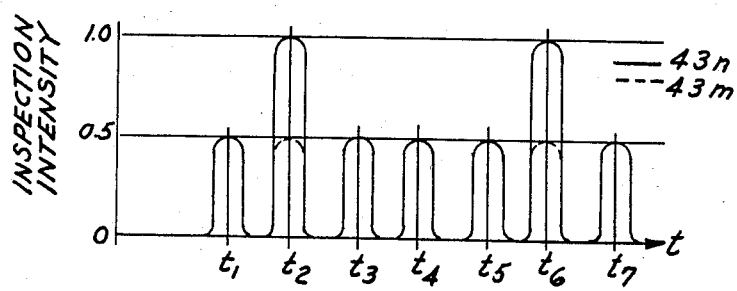
Figure 8D:
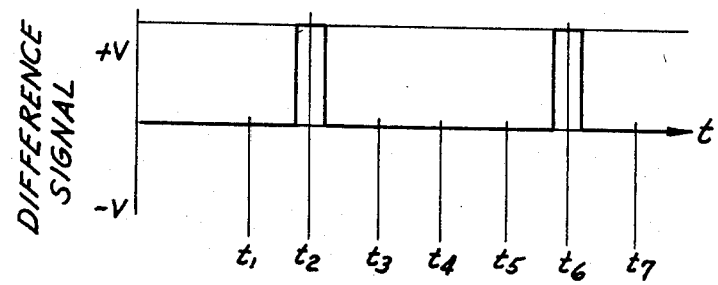

FIGS. 8A–8D and 9A–9D, which are respectively similar to FIGS. 4A–4D and 5A–5D, illustrate another embodiment of the invention. FIGS. 8A and 8B, optical attenuation density in outer zones 58C and 62C of the filter plate 50C are substantially zero or transparent. Within central zone 60C, the optical density is substantially 50 percent.

In operation of this embodiment, the light intensity sensed by pixel 43n will vary as its field of view is refracted from the midline of the central zone 60C by the blister 64. Starting at scan time $t_1$, just before the blister 64 enters the field of view of the pixel 43n, the intensity sensed by pixel 43n is at about the 50 percent level since the field of view of the pixel 43n is incident the midline of central zone 60C. Thus, the corresponding difference signal at scan time $t_1$ is essentially zero since the intensities sensed by adjacent pixels 43n and 43m are substantially the same. However, at scan time $t_2$, just as the leading edge of the blister 64 enters the field of view of pixel 43n while moving in direction 66 with respect to the stationery filter plate 50C and camera 42, the intensity sensed by pixel 43n increases to about the 100 percent level because the leading edge of the blister 64 optically refracts the field of view of pixel 43n into the essentially transparent outer zone 58C. The corresponding difference signal at scan time $t_2$ is a substantially positive value because the intensity sensed by pixel 43n is substantially greater than that sensed by pixel 43m. At scan times $t_3$–$t_5$, when the leading edge of the blister 64 moves further into the field of view of pixel 43n, the intensity sensed by pixel 43n decreases to about the 50 percent level. Thus, the corresponding difference signal at scan times $t_3$–$t_5$ are substantially zero. At scan time $t_6$, when the trailing edge of the blister 64 moves fully into the field of view of pixel 43n, the intensity sensed returns to 100 percent because the trailing edge of the blister 64 refracts the field of view into outer zone 62C which is essentially transparent. Thus, the corresponding difference signal at scan time $t_6$ has a substantially positive value because the intensity sensed by pixel 43n is substantially greater than that sensed by pixel 43m. At scan time $t_7$, after the trailing edge of the blister 54 moves out of the field of view of the pixel 43n, the intensity sensed is again at about the 50 percent level because the field of view of pixel 43n is incident the midline of central zone 60C rather than being refracted by a defect. Thus, the corresponding difference signal at scan time $t_7$ is essentially zero since the intensities sensed by pixels 43n and 43m are substantially the same.

As can be seen, the difference signals associated with a blister or any refractive defect in this embodiment produce a computer-identifiable signature which comprises a pair of peak-positive values. The information processor 56 determines the size of the blister 64 by using the connectivity analysis referred to above which provides an indication of the transverse dimension of the blister 64 by counting the number of scans between the peak-positive difference signals corresponding to the leading and trailing edge of the blister 64. The information processor 56 is programmed to provide a reject signal 32 when the number of scans exceeds a predetermined threshold indicating the presence of a large blister, so that containers with large blisters are rejected and containers with small blisters are not rejected as being commercially acceptable. The same analysis would be used and the same signature would be obtained if the blister 64 were large enough to interfere with the field of view of several pixels 43. A similar signature would be obtained for each pixel varying only in transverse length.

Referring to FIGS. 9A to 9D, an opaque defect or stone 68 is shown in the field of view of pixel 43n. In operation, the light intensity sensed by pixel 43n will vary as its field of view is blocked from the midline of the central zone 60C by the stone 68. At scan time $t_2$, just as the leading edge of the stone 68 enters the field of view of pixel 43n, the intensity sensed by pixel 43n drops to zero because the stone is opaque. Thus, the corresponding difference signal at scan time $t_2$ has a substantially negative value because the intensity sensed by pixel 43n is substantially less than that sensed by pixel 43m. The same analysis applies to the light intensity sensed by pixel 43n at scan times $t_3$ to $t_6$. Thus, the signature produced by the stone 68 is readily distinguishable from the signature produced by the blister 64; the signature of a blister is flanked by peak-positive values while the signature of a stone consists solely of peak-negative values. Thus, this embodiment of the invention permits the SID to detect the presence of an opaque defect, while at the same time being able to detect refractive defects by optical enhancement and further distinguish between small and large refractive defects.

Figure 7A:
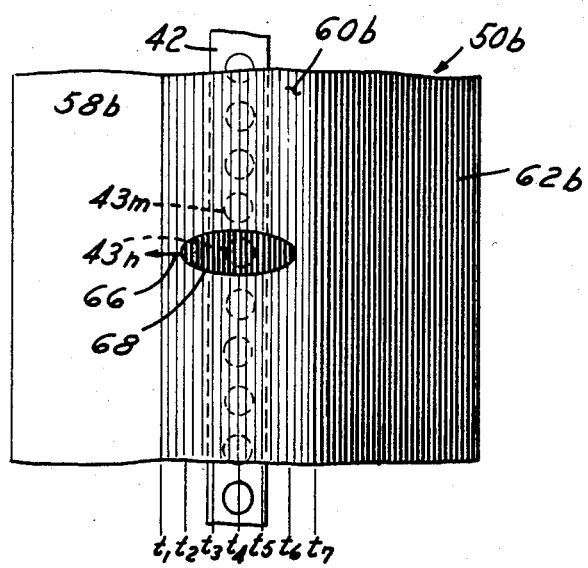
Figure 7B:
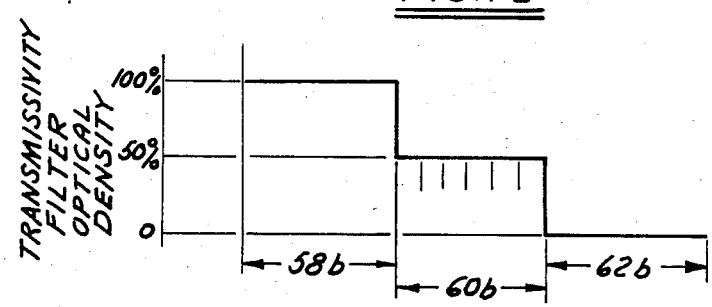
Figure 7C:
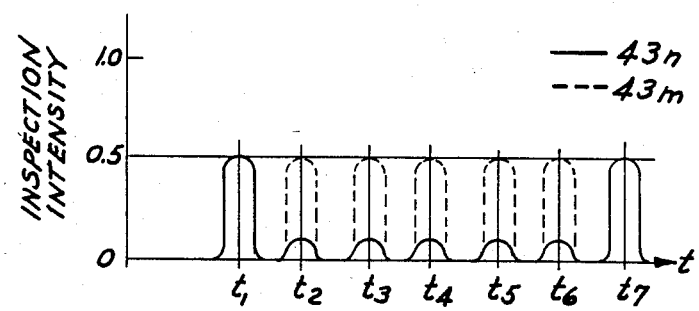
Figure 7D:
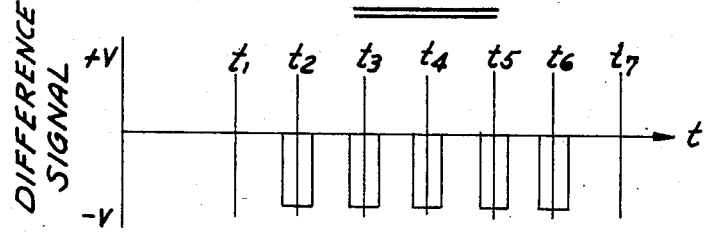
Figure 9A:
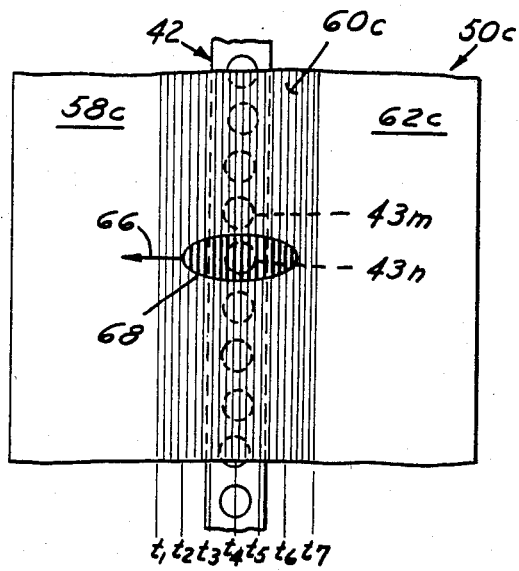
Figure 9B:
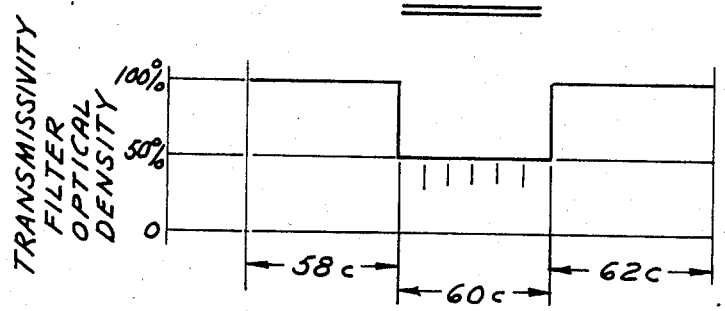
Figure 9C:
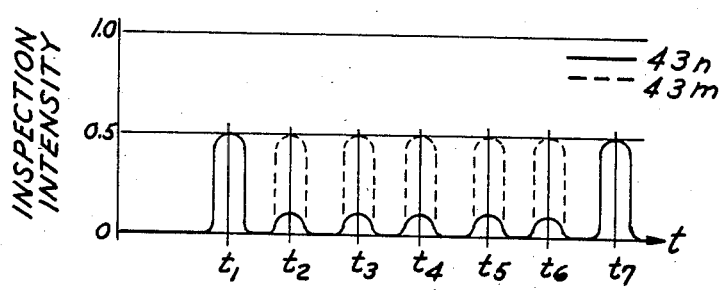
Figure 9D:
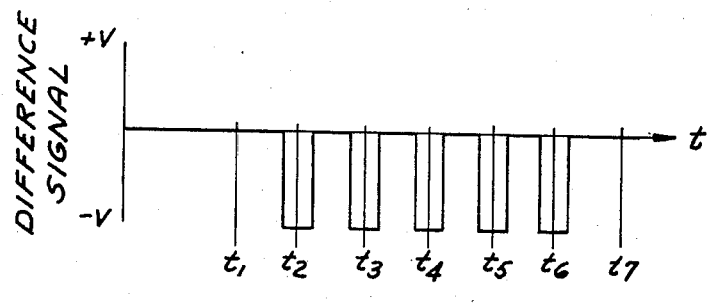

Thus, it will be appreciated that the various embodiments of the invention herein disclosed provide not only for detection of opaque and refractive defects, but also provide for discrimination between such defects both on the basis of type and on the basis of size. It will be appreciated, of course, that the blister defects 64 in FIGS. 4A, 6A and 8A, and the stone defects in FIGS. 5A, 7A and 9A are illustrated as being of identical size for purposes of comparison. It will also be appreciated that sensitivity of the various embodiments of the invention to refractive or opaque defects of varying size may be controlled by varying the scan increments, for example, by varying the transverse dimensions D, W and E of filter zones 58, 60 and 62 in FIG. 3, by varying the dimension C between the camera centerline and the contiguous edges of zones 58, 60 and/or by varying the overall effective width SW of light source 40. It is presently preferred that each filter zone 58, 60, 62 possess uniform attenuation density in the longitudinal direction—i.e. in the vertical direction of the container axis—although such density may be varied in the longitudinal direction in accordance with the principles of the referenced application Ser. No. 424,687 if desired. For containers having a narrowing neck (FIG. 2), it is contemplated that the width W of the intermediate zone opposite the neck will increase with decreasing neck diameter.

Sampler electronics 54 and information processor 56 (FIG. 2) are disclosed in greater detail in the aforementioned U.S. Pat. Nos. 4,378,494 and 4,378,495.

As previously indicated, the broad concept of inspecting and sorting transparent containers by directing diffused light energy through a container sidewall to provide an intensity gradient which varies as a predetermined function of position in a given direction, as well as specific implementation of this concept in which the intensity varies in the longitudinal direction parallel to the container axis, is the subject of the aforementioned copending U.S. application Ser. No. 424,687 which has been incorporated herein by reference.

The invention claimed is:

1. A method of sorting transparent containers having defects in the container sidewalls, which defects affect optical transmission characteristics of the container sidewalls, said method comprising the steps of:
   (a) rotating a said container about its central axis,
   (b) directing a source of diffused illumination through the sidewall of the containers, with said illumination varying in intensity in a direction transverse to said axis as a predetermined function of position across said source in said transverse direction,
   (c) positioning a camera which inlcudes a plurality of light responsive elements disposed in a linear array such that said array extends in a direction parallel to said axis so as to define a field of view parallel to said axis,
   (d) identifying defects in the container sidewall as a function of differences in light energy sensed by adjacent ones of said light responsive elements by:
   (d1) scanning said plurality of light responsive elements at increments of container rotation to develop a series of pixel signals from each said element corresponding to intensity of light at each said element at each said scan increment,
   (d2) comparing pixel signals from each said element at each said increment to at least one pixel signal from the same said element at a differing said increment, and
   (d3) identifying container sidewall defects as a function of differences between said compared signals, and
   (e) rejecting a container in which a defect is so identified, whereby a defective container is sorted from commercially acceptable containers.

2. The method set forth in claim 1 wherein said step (b) includes the step of filtering the intensity of diffused illumination directed through the container sidewall by said source so as to define at least two zones in which intensity of illumination varies as differing functions of position in said transverse direction.

3. The method set forth in claim 2 wherein said step (b) comprises the step of filtering the intensity of diffused illumination directed through the container sidewall by said source so as to define three laterally adjacent zones across the transverse dimension of said source in each of which the intensity of illumination varies as a predetermined function of transverse position which differs from that of the next-adjacent zone.

4. The method set forth in claim 3 wherein said step (b) comprises the steps of (b1) filtering the intensity of diffused illumination in the outside ones of said zones to possess substantially uniform intensities with transverse position, and
   (b2) filtering the intensity of diffused illumination in the intermediate one of said zones to possess an intensity function with transverse position which differs from both of said substantially uniform intensities.

5. The method set forth in claim 4 wherein said substantially uniform intensities in said outside ones of said zones are at differing intensity levels, and wherein intensity in said intermediate zone is between said differing intensity levels.

6. The method set forth in claim 4 or 5 wherein intensity in said intermediate zone varies as a uniform function of transverse position across said intermediate zone between said substantially uniform intensities in said outside zones.

7. The method set forth in claim 6 wherein intensity in said intermediate zone varies as a substantially linear function of transverse position across said intermediate zone.

8. The method set forth in claim 3 comprising the additional step of (f) controlling the dimensions of said zones in a direction transverse to said axis and position of said light responsive means with respect to said zones to detect sidewall defects of predetermined minimum size and character.

9. The method set forth in claim 4 wherein said intensity of diffused illumination in said intermediate one of said zones is substantially uniform with position transversely of said axis and is unequal to the intensity in said outside ones of said zones.

10. The method set forth in claim 9 wherein said step (b) comprises the step of filtering said diffused illumination in said outside ones of said zones to provide unequal, substantially uniform intensisties in said outside zones.

11. The method set forth in claim 10 wherein said step (b) comprises the additional step of filtering intensity in said intermediate one of said zones to a level intermediate the intensities in said outside zones.

12. The method set forth in claim 9 wherein said step (b) comprises the step of filtering said diffused illumination in said outside ones of said zones to provide equal, substantially uniform intensities in said outside zones.

13. The method set forth in claim 12 wherein said step (b) comprises the additional step of filtering intensity in said intermediate one of said zones to be less than in said outside zones.

14. The method set forth in claim 3 wherein said step (d2) comprises the step of comparing each said pixel signal with a plurality of pixel signals from the same said element, and
wherein said step (d3) includes the step of indentifying types and sizes of container defects as a function of differences between said compared signals.

15. Apparatus for detecting defects in the sidewalls of transparent containers and sorting containers having defects so detected comprising
means for positioning a container and for rotating the container about its central axis,
a light source for directing diffused illumination through the sidewall of a container so positioned and rotated, said diffused illumination having an intensity which varies transversely of said axis as a predetermined function of position across the width of said source,
light sensing means positioned to receive light energy transmitted through the container sidewall,
means for detecting sidewall defects in the container as a function of variations in intensity of light received at said sensing means between successive increments of container rotation, and
means for rejecting a container in which a defect is so detected.

16. The apparatus set forth in claim 15 wherein said source provides said diffused illumination in three zones laterally adjacent to each other in a direction transverse to said axis, each of said zones including means for attenuating intensity of light energy transmitted therethrough as a predetermined function of position in said transverse direction, each said function differing from that associated with the next-adjacent zone.

17. The apparatus set forth in claim 16 wherein intensities of diffused illumination transmitted through the outside ones of said zones are substantially constant with transverse position, and
wherein the intensity of diffused illumination transmitted through the intermediate said zone is different from said substantially constant intensities.

18. The apparatus set forth in claim 17 wherein said substantially uniform intensities in said outside zones are at differing intensity levels, and wherein intensity in said intermediate zone is between said differing intensity levels.

19. The apparatus set forth in claim 17 or 18 wherein intensity in said intermediate zone varies as a uniform function of transverse position across said intermediate zone between said substantially uniform intensities in said outside zones.

20. The apparatus set forth in claim 19 wherein intensity in said intermediate zone varies as a substantially linear function of transverse position across the intermediate zone.

21. The apparatus set forth in claim 16 wherein said light sensing means comprises a plurality of light responsive elements disposed in a linear array substantially parallel to said axis, and
wherein said detecting means comprises means responsive to said elements for comparing intensity of light energy received by each of said elements at each increment of container rotation with the intensity of light received by the next adjacent said element, and means responsive to said comparing means for identifying defects in the container sidewall as a function of a difference in said intensities.

22. The apparatus set forth in claim 21 wherein said identifying means comprises means responsive to said comparing means for distinguishing among kinds of defects as a function of said difference.

23. The apparatus set forth in claim 15 further comprising conveyor means for feeding containers sequentially to and from said positioning and rotating means, and means for selectively actuating said rejecting means to divert containers from said conveyor means when a said defect is detected.

24. The apparatus set forth in claim 17 wherein intensity of illumination in said intermediate zone is substantially constant transversely of said axis and is unequal to intensities in said outside zones.

25. The apparatus set forth in claim 24 wherein diffused illuminations in said outside zones posses unequal, substantially constant intensities transversely of said axis.

26. The apparatus set forth in claim 25 wherein intensity in the said intermediate zone is intermediate said unequal intensities in said outside zones.

27. The appratus set forth in claim 24 wherein said substantially uniform intensities in said outside zones are substantially equal, and wherein intensity in said intermediate zone is substantially uniform with transverse position and unequal to intensities in said outside zones.

* * * * *